United States Patent
Umebayashi

(10) Patent No.: US 12,157,077 B2
(45) Date of Patent: Dec. 3, 2024

(54) COMBINED FIBER NONWOVEN FABRIC, LAMINATE, FILTRATION MEDIUM FOR FILTER AND METHOD THEREOF

(71) Applicants: JNC CORPORATION, Tokyo (JP); JNC FIBERS CORPORATION, Tokyo (JP)

(72) Inventor: You Umebayashi, Shiga (JP)

(73) Assignees: JNC CORPORATION, Tokyo (JP); JNC FIBERS CORPORATION, Tokyo (JP)

( * ) Notice: Subject to any disclaimer, the term of this patent is extended or adjusted under 35 U.S.C. 154(b) by 5 days.

(21) Appl. No.: 16/758,863

(22) PCT Filed: Oct. 23, 2018

(86) PCT No.: PCT/JP2018/039340
§ 371 (c)(1),
(2) Date: Jun. 16, 2020

(87) PCT Pub. No.: WO2019/082887
PCT Pub. Date: May 2, 2019

(65) Prior Publication Data
US 2021/0236971 A1    Aug. 5, 2021

(30) Foreign Application Priority Data
Oct. 25, 2017  (JP) ................. 2017-205986

(51) Int. Cl.
*B01D 39/16* (2006.01)
*D04H 1/4382* (2012.01)
*D04H 1/728* (2012.01)

(52) U.S. Cl.
CPC ..... *B01D 39/1623* (2013.01); *D04H 1/43835* (2020.05); *D04H 1/43838* (2020.05); *D04H 1/728* (2013.01); *B01D 2239/025* (2013.01); *B01D 2239/0618* (2013.01); *B01D 2239/0631* (2013.01); *B01D 2239/0636* (2013.01); *B01D 2239/064* (2013.01); *B01D 2239/065* (2013.01); *B01D 2239/10* (2013.01); *B01D 2239/1233* (2013.01); *B01D 2239/1291* (2013.01); *D10B 2505/04* (2013.01)

(58) Field of Classification Search
None
See application file for complete search history.

(56) References Cited

U.S. PATENT DOCUMENTS

| | | | |
|---|---|---|---|
| 2008/0182167 A1* | 7/2008 | Kritzer | B32B 27/08 429/129 |
| 2009/0272086 A1* | 11/2009 | Hsiao | D01D 5/0069 55/528 |

FOREIGN PATENT DOCUMENTS

| | | | | |
|---|---|---|---|---|
| CN | 103717796 | | 4/2014 | |
| CN | 106868712 A | * | 6/2017 | .......... D01D 5/0007 |
| JP | 2005218909 | | 8/2005 | |
| JP | 2006341233 | | 12/2006 | |
| JP | 2009057655 | | 3/2009 | |
| JP | 2009275310 | | 11/2009 | |
| JP | 2010509056 | | 3/2010 | |
| JP | 2010156063 | | 7/2010 | |
| JP | 2012221600 | | 11/2012 | |
| JP | 2012221600 A | * | 11/2012 | |
| JP | 2014200701 | | 10/2014 | |
| JP | 2018184673 | | 11/2018 | |
| WO | 2012017953 | | 2/2012 | |
| WO | WO-2012017953 A1 | * | 2/2012 | ........ H01M 50/4295 |
| WO | 2014168066 | | 10/2014 | |
| WO | 2017047185 | | 3/2017 | |

OTHER PUBLICATIONS

Bin Ding, Eiji Kimura, Tomokazu Sato, Shiro Fujita, Seimei Shiratori, Fabrication of blend biodegradable nanofibrous nonwoven mats via multi-jet electrospinning, Polymer, vol. 45, Issue 6, 2004, pp. 1895-1902 (Year: 2004).*

Jian-Yi Zheng, et al., "The Effect of Surfactants on the Diameter and Morphology of Electrospun Ultrafine Nanofiber", Journal of Nanomaterials, vol. 2014, Article ID 689298, 9 p. 2014. (Year: 2014).*

Polypropylene: 9003-07-0. ChemicalBook. (n.d.). Retrieved Sep. 26, 2022, from https://www.chemicalbook.com/ChemicalProductProperty_EN_CB8366058.htm (Year: 2022).*

Polyvinylidene fluoride: 24937-79-9. Chemical Book. (n.d.). Retrieved Sep. 26, 2022, from https://www.chemicalbook.com/ChemicalProductProperty_EN_CB6313270.htm (Year: 2022).*

Polybutene: 9003-28-5. ChemicalBook. (n.d.). Retrieved Sep. 26, 2022, from https://www.chemicalbook.com/ChemicalProductProperty_EN_CB0316097.htm (Year: 2022).*

"International Search Report (Form PCT/ISA/210) of PCT/JP2018/039340", mailed on Jan. 15, 2019, with English translation thereof, pp. 1-4.

Office Action of China Counterpart Application, with English translation thereof, issued on Nov. 1, 2021, pp. 1-15.

* cited by examiner

Primary Examiner — Jason M Greene
Assistant Examiner — Eric J McCullough
(74) Attorney, Agent, or Firm — JCIPRNET

(57) ABSTRACT

A filtration medium for a filter, having high dust collection efficiency, low pressure loss, a long service life and sufficient processing strength into a filter. A combined fiber nonwoven fabric includes first fibers having a mean fiber diameter of less than 200 nanometers, and second fibers having a mean fiber diameter in the range of 200 to 5000 nanometers, in which basis weight of the combined fiber nonwoven fabric is in the range of 2.1 to 15.0 g/m$^2$.

6 Claims, No Drawings

COMBINED FIBER NONWOVEN FABRIC, LAMINATE, FILTRATION MEDIUM FOR FILTER AND METHOD THEREOF

CROSS-REFERENCE TO RELATED APPLICATION

This application is a 371 application of the international PCT application serial no. PCT/JP2018/039340, filed on Oct. 23, 2018, which claims the priority benefit of Japan application no. 2017-205986, filed on Oct. 25, 2017. The entirety of each of the above-mentioned patent applications is hereby incorporated by reference herein and made a part of this specification.

TECHNICAL FIELD

The invention relates to a combined fiber nonwoven fabric and a filtration medium for a filter, formed of a laminate containing the combined fiber nonwoven fabric.

BACKGROUND ART

A nonwoven fabric sheet has been so far used in many cases as a filtration medium for an air filter for removing fine dust such as pollen and particulate matter. Such a filtration medium for a filter has been required to have performance of collecting dust with high efficiency (high collection efficiency) and performance of low resistance when a fluid passes through the filtration medium (low pressure loss).

Moreover, as a method for achieving the high collection efficiency and the low pressure loss, a filtration medium using ultrafine fibers has been proposed so far. For example, Patent literature No. 1 proposes a filtration medium provided with an ultrafine fiber layer having a mean fiber diameter of 170 nanometers or less. However, from such a filtration medium, a filter having low basis weight, high collection efficiency and low pressure loss is obtained, but the filtration medium forms a dense matrix body, and therefore extension of a service life of the filter obtained has been difficult. Moreover, the mean fiber diameter is as significantly fine as 170 nanometers, and therefore processing strength (strength upon processing) into the filter becomes insufficient, and a problem of easily breaking the filter has remained.

As a method for solving the problems of the service life extension and the processing strength in the filtration medium using the ultrafine fibers, a (combined fiber) filtration medium in which the ultrafine fibers are mixed with fibers thicker than the ultrafine fibers has been proposed. For example, Patent literature No. 2 proposes an ultrafine fiber nonwoven fabric in which electrostatic spun fibers formed by electrostatic spinning are combined and mixed with melt-blown fibers formed by a melt-blown method. However, fiber production methods using different principles are combined, and therefore such an art has a problem in which a production apparatus becomes complicated and production is difficult. Moreover, for example, Patent literature No. 3 proposes a filtration medium having a basis weight of 0.1 to 2.0 g/m² of nanofibers have, and containing fine fiber-diameter nanofibers having a fiber diameter of 10 to 100 nanometers and a proportion of the number of fibers of 10 to 90%, thick fiber-diameter nanofibers having a fiber diameter of 140 to 1000 nanometers and a proportion of the number of fibers of 10 to 90%, and fibers having a fiber diameter of more than 100 nanometers and less than 140 nanometers and a proportion of the number of fibers of 0 to 10%. However, in the filtration medium having such a fiber configuration, a filter service life and processing strength into the filter become insufficient, and therefore further improvement is required.

CITATION LIST

Patent Literature

Patent literature No. 1: JP 2006-341233 A.
Patent literature No. 2: JP 2009-57655 A.
Patent literature No. 3: JP 2014-200701 A.

SUMMARY OF INVENTION

Technical Problem

As described above, the invention provides a filtration medium for a filter, having high dust collection efficiency, low pressure loss, a long service life and sufficient processing strength into a filter.

Solution to Problem

The present inventors have diligently continued to conduct study for solving the problems described above. As a result, the present inventors have found that a filtration medium for a filter can be provided by using a combined fiber nonwoven fabric containing first fibers having a mean fiber diameter of less than 200 nanometers, and second fibers having a mean fiber diameter in the range of 200 to 5000 nanometers, and the combined fiber nonwoven fabric in which basis weight of the combined fiber nonwoven fabric is 2.1 to 15.0 g/m², dust collection efficiency is high, pressure loss is low, a service life is long, and processing strength into a filter is sufficient, and thus have completed the invention.

The invention has a structure as described below.

Item 1. A combined fiber nonwoven fabric, comprising first fibers having a mean fiber diameter of less than 200 nanometers; and second fibers having a mean fiber diameter in the range of 200 to 5000 nanometers, wherein basis weight of the combined fiber nonwoven fabric is in the range of 2.1 to 15.0 g/m².

Item 2. The combined fiber nonwoven fabric according to item 1, wherein a ratio of the number of the first fibers to the second fibers is in the range of 80:20 to 98:2.

Item 3. The combined fiber nonwoven fabric according to any one of items 1 to 2, wherein a coefficient of variation of a fiber diameter of the first fibers and a coefficient of variation of a fiber diameter of the second fibers are 0.5 or less.

Item 4. The combined fiber nonwoven fabric according to any one of items 1 to 3, wherein a melting point of the first fibers is higher than a melting point of the second fibers by 10° C. or more.

Item 5. A laminate, in which the combined fiber nonwoven fabric according to any one of items 1 to 4 is laminated on at least one side of a base material having a specific volume of 5 g/cm³ or less.

Item 6. A filtration medium, using the combined fiber nonwoven fabric according to any one of items 1 to 4 or the laminate according to item 5.

Item 7. A method of producing a combined fiber nonwoven fabric, comprising: a step of forming fibers by electrostatic spinning of a first spinning solution for forming first fibers and a second spinning solution for forming second fibers; and a step of mixing the first fibers formed with the second fibers formed to obtain a nonwoven fabric.

Advantageous Effects of Invention

A filtration medium for a filter, having high dust collection efficiency, low pressure loss, a long service life and sufficient processing strength into a filter can be provided by using a combined fiber nonwoven fabric having the above-described configuration according to the invention.

DESCRIPTION OF EMBODIMENTS

Hereinafter, the invention will be described in detail.

A combined fiber nonwoven fabric of the invention has features of containing first fibers having a mean fiber diameter of less than 200 nanometers, and second fibers having a mean fiber diameter in the range of 200 to 5000 nanometers. A filtration medium for a filter, having high dust collection efficiency, low pressure loss, a long service life and sufficient processing strength into a filter can be provided as a filtration medium for a filter by applying such a fiber configuration.

The mean fiber diameter of the first fibers is less than 200 nanometers, preferably 10 to 100 nanometers, and further preferably 30 to 80 nanometers. If the mean fiber diameter of the first fibers is less than 200 nanometers, a specific surface area of the combined fiber nonwoven fabric obtained is increased, and when the combined fiber nonwoven fabric is used as the filtration medium for the filter, high filter performance such as having the low pressure loss and the high collection efficiency is obtained. If the mean fiber diameter of the first fibers is 100 nanometers or less, further excellent filter performance is obtained. If the mean fiber diameter of the first fibers is 80 nanometers or less, still further excellent filter performance is obtained. Meanwhile, as the fiber diameter is decreased, strength per fiber is decreased, which has a possibility of causing breaking of the fibers during processing into the filter or during use. However, if the mean fiber diameter of the first fibers is 10 nanometers or more, satisfactory single fiber strength is obtained. If the mean fiber diameter is 30 nanometers or more, sufficient single fiber strength is obtained. A coefficient of variation of the fiber diameter of the first fibers is not particularly limited, and is preferably 0.5 or less, and further preferably 0.3 or less. If the coefficient of variation of the first fibers is 0.5 or less, excellent filter performance is obtained. If the coefficient of variation of the first fibers is 0.3 or less, further excellent filter performance is obtained.

The mean fiber diameter of the second fibers is in the range of 200 to 5000 nanometers, preferably in the range of 400 to 2000 nanometers, and further preferably in the range of 600 to 1500 nanometers. If the mean fiber diameter of the second fibers is 200 nanometers or more, strength of the combined fiber nonwoven fabric is increased, and processability is improved, and also an interfiber distance between the first fibers is increased. When the nonwoven fabric is used as the filtration medium for the filter, the filter is hard to cause clogging by collected dust, and the service life of the filter can be extended. If the mean fiber diameter of the second fibers is 5000 nanometers or less, an effect in accordance with intended use is obtained even with comparatively low basis weight, and thickness reduction and improvement in productivity of the filter can be achieved. If the mean fiber diameter of the second fibers is in the range of 400 to 2000 nanometers, high strength, service life extension, basis weight reduction and thickness reduction of the filter can be achieved with a satisfactory balance. If the mean fiber diameter of the second fibers is in the range of 600 to 1500 nanometers, the above characteristics can be developed with an excellent balance. A coefficient of variation of the fiber diameter of the second fibers is not particularly limited, and is preferably 0.5 or less, and further preferably 0.3 or less. If the coefficient of variation of the second fibers is 0.5 or less, excellent filter performance is obtained with low basis weight, and therefore thickness reduction and size reduction of the filter can be achieved. If the coefficient of variation is 0.3 or less, further thickness reduction and size reduction can be achieved.

The proportion (ratio of the number) of the first fibers to the second fibers is not particularly limited, and the ratio of the number of the first fibers to the second fibers is preferably in the range of 80:20 to 98:2, and further preferably in the range of 85:15 to 95:5. If the ratio of the number of the first fibers to the second fiber is 80:20 or more, the filter having the high collection efficiency is obtained with the filtration medium having comparatively low basis weight, and reduction in the pressure loss, thickness reduction and improvement in productivity can be achieved. If the ratio is 98:2 or less, service life extension and high strength can be achieved.

A resin for the first fibers and the second fibers in the invention is not particularly limited, and specific examples thereof can include a polymer material such as polyvinyl alcohol, polyethylene glycol, polyethylene oxide, polyvinyl pyrrolidone, polyethylene, polypropylene, polyethylene terephthalate, polylactic acid, polyamide, polyurethane, polystyrene, polysulfone, polyethersulfone, polyvinylidene fluoride, polyacrylonitrile, polymethyl methacrylate, polyglycolic acid, polycaprolactone, polyvinyl acetate, polycarbonate, polyimide, polyether imide, cellulose, a cellulose derivative, chitin, chitosan, collagen, gelatin and a copolymer thereof. Weight average molecular weight of the resin is not particularly limited, and is preferably in the range of 10,000 to 10,000,000, and further preferably in the range of 50,000 to 5,000,000, and still further preferably in the range of 100,000 to 1,000,000. If the weight average molecular weight is 10,000 or more, the resin is excellent in fiber-forming properties of the first fibers and the second fibers, and therefore such a case is preferred. If the weight average molecular weight is 10,000,000 or less, the resin is excellent in solubility and thermoplasticity, and processing is facilitated, and therefore such a case is preferred.

A combination of the resins constituting the first fibers and the second fibers of the invention is not particularly limited, and a same kind of resins may be used, or different kinds of resins may be combined. A combination of the different kinds of resins is not particularly limited, and specific examples thereof can include a non-elastomer resin/an elastomer resin, a high melting point resin/a low melting point resin, a high crystalline resin/a low crystalline resin and a hydrophilic resin/a water-repellent resin. For example, the first fibers composed of the non-elastomer resin and the second fibers composed of the elastomer resin are combined, whereby the combined fiber nonwoven fabric can be provided with stretchability, and upon pleating the nonwoven fabric into an air filter use, an effect of suppressing breaking by bending is produced. The elastomer resin is not particularly limited, and specific examples thereof can include a polyolefin-based elastomer, a polyester-based elastomer, a polyurethane-based elastomer and a polyamide-based elastomer. Moreover, the first fibers composed of the high melting point resin is combined with the second fibers composed of the low melting point resin, the resulting fibers are heat-treated at a temperature of less than a melting point of the first fibers and a melting point or higher of the second fibers to fuse the first fibers with the second fibers or between the second fibers, whereby processing strength can be increased while maintaining the collection efficiency of the combined fiber nonwoven fabric obtained. Further, upon integration with a base material or another layer, the second fibers and the base material or another layer are fused with each other, and therefore strength of the integrated laminate can be further increased. The combination of the high melting point resin/the low melting point resin is not particularly limited, and a melting point difference is preferably 10° C. or more, and further preferably 20° C. or more. The combination of such resins is not particularly limited, and specific examples thereof can include polyvinylidene fluoride/a copolymer of vinylidene fluoride and hexafluoropropylene, nylon 66/nylon 6, poly-L-lactic acid/poly-D,L-lactic acid, polypropylene/polyethylene, polyethylene terephthalate/polyethylene, and polyethylene terephthalate/polypropylene. Moreover, the first fibers composed of the high crystalline resin is combined with the second fibers composed of the low crystalline resin, whereby the combined fiber nonwoven fabric can be provided with dimensional stability, and when the nonwoven fabric is used as the filtration medium for the filter, the filter performance can be maintained even under an environment of a wide range of temperature and humidity. The high crystalline resin is not particularly limited, and specific examples thereof can include polyvinylidene fluoride, nylon 6, nylon 66, polyethylene, polypropylene, polyethylene terephthalate, polylactic acid, polyvinyl alcohol and polyethylene glycol. The low crystalline resin is not particularly limited, and specific examples thereof can include a copolymer of vinylidene fluoride and hexafluoropropylene, a copolymer of ethylene and propylene, poly-D,L-lactic acid, polystyrene, polysulfone, polyethersulfone, polycarbonate, polymethyl methacrylate, polyurethane and polyvinyl acetate.

In order to have the high collection efficiency, the low pressure loss, the long service life and the sufficient processing strength into the filter as the filtration medium for the filter, the basis weight of the combined fiber nonwoven fabric of the invention is necessarily in the range of 2.1 to 15.0 g/m², preferably in the range of 3.0 to 12.0 g/m², and further preferably in the range of 6.0 to 12.0 g/m². If the basis weight is 2.1 g/m² or more, as the filtration medium for the filter, the long service life, the high collection efficiency, the high processing strength into the filter can be achieved, and if the basis weight is 3.0 g/m² or more, as the filtration medium for the filter, the collection efficiency, the pressure loss, the service life and the processing strength into the filter can be satisfied with an excellent balance. If the basis weight is 6.0 g/m² or more, as the filtration medium for the filter, the collection efficiency, the pressure loss, the service life and the processing strength to the filter can be satisfied with a particularly excellent balance. Moreover, if the basis weight is 15.0 g/m² or less, as the filtration medium for the filter, the pressure loss can be decreased. If the basis weight is 12.0 g/m² or less, the pressure loss can be further decreased.

The combined fiber nonwoven fabric of the invention may be integrally laminated on the base material such as another nonwoven fabric, a woven fabric, a net or a microporous film, and is not particularly limited thereto. The laminate having composite characteristics of the combined fiber nonwoven fabric and the base material can be obtained by integrally laminating the combined fiber nonwoven fabric on the basic material. When the laminate is used as the filtration medium for the air filter, from viewpoints of processability and air permeability, the base material is preferably a nonwoven fabric. Specific examples of the characteristics of the base material include provision of mechanical strength, wear resistance, pleating processability and adhesion characteristics, and the base material having such characteristics can be appropriately selected according to the intended use or form of the combined fiber nonwoven fabric. A method of integrally laminating the combined fiber nonwoven fabric on the base material is not particularly limited, and the combined fiber nonwoven fabric and the base material separately produced may be integrated by using an adhesive or thermal fusion, or may be integrated by directly spinning the combined fiber nonwoven fabric on the base material, or may be integrated by directly spinning the combined fiber nonwoven fabric on the base material and then heat treating the resulting material.

The basis weight of the base material is not particularly limited, and the basis weight is preferably 15 g/m² or more, further preferably 30 g/m² or more, and still further preferably 60 g/m² or more. If the basis weight of the base material is 15 g/m² or more, shrinkage, wrinkling, curl or the like of the combined fiber nonwoven fabric is suppressed and the processing strength can be provided, and if the basis weight of the base material is 30 g/m² or more, the satisfactory processing strength can be provided. If the basis weight of the base material is 60 g/m² or more, the sufficient processing strength can be provided. The specific volume of the base material is not particularly limited, and is preferably 5 cm³/g or less, and further preferably 3 cm³/g or less. If the specific volume of the base material is 5 cm³/g or less, the wear resistance on a surface of the combined fiber nonwoven fabric of the laminate is improved, and reduction of characteristics upon processing can be suppressed. If the specific volume of the base material is 3 cm³/g or less, reduction of the characteristics can be sufficiently suppressed.

A raw material constituting the base material may be appropriately selected, when necessary, and is not particularly limited. For example, when a polyolefin-based raw material such as polypropylene and polyethylene is used as the raw material, the resulting material has a feature of being excellent in chemical resistance, and can be preferably used in an application such as a liquid filter requiring the chemical resistance. Moreover, for example, when a polyester-based raw material such as polyethylene terephthalate, polybutylene terephthalate, polylactic acid or a copolymer containing the above compounds as a major constituent is used as the raw material, the resulting material is excellent in pleating characteristics, and therefore can be preferably used in an application such as an air filter requiring pleating. The polyester-based raw material has high wettability with an adhesion component such as hot melt, and can be preferably used when a product is processed by hot melt adhesion. A base material in which a polypropylene-based or polyester-based raw material constitutes a surface allows adhesion by ultrasonic waves, and therefore can be preferably used.

When the combined fiber nonwoven fabric is integrated with the base material by heat treatment, a nonwoven fabric formed of thermal fusible conjugate fibers composed of a low melting point component and a high melting point component is preferably used as the base material, but is not particularly limited thereto. A combination, a conjugate form and a cross-sectional shape of the raw materials of the thermal fusible conjugate fibers are not particularly limited, and a publicly-known art can be used. Specific examples of the combination of the raw materials include a combination of copolymerized polyethylene terephthalate and polyethylene terephthalate, a combination of copolymerized polyethylene terephthalate and polypropylene, a combination of high density polyethylene and polypropylene, a combination of high density polyethylene and polyethylene terephthalate, a combination of copolymerized polypropylene and polypropylene, a combination of copolymerized polypropylene and polyethylene terephthalate and a combination of polypropylene and polyethylene terephthalate. Further, in consideration of ease of availability of the raw material or the like, specific examples thereof can preferably include a combination of copolymerized polyethylene terephthalate and polyethylene terephthalate, a combination of high density polyethylene and polypropylene and a combination of high density polyethylene and polyethylene terephthalate. Moreover, specific examples of the conjugate form of a cross section include a sheath-core type, an eccentric sheath-core type and a side-by-side type. The cross-sectional shape of the fibers is not particularly limited, either, and in addition to a general round shape, all cross-sectional shapes such as an elliptic shape, a hollow shape, a triangle, a quadrangle and a profile cross section including a double quatrefoil can be adopted.

A method of producing the nonwoven fabric formed of the thermal fusible conjugate fibers is not particularly limited, and a publicly-known producing method such as a carding method, a paper-making method, an air-laid method, a melt-blown method or a spunbond method can be used. A fiber adhesion method upon processing the fibers into the nonwoven fabric is not particularly limited, either, and specific examples thereof include thermal fusion by air-through processing, thermocompression bonding by embossing, fiber interlacing by needle punching or spunlace processing and chemical bonding by an adhesive.

In the laminate of the invention, at least one layer selected from the group of a nonwoven fabric, a woven fabric, a net and a microporous film may be further laminated on at least one side or both sides thereof. At least one layer selected from the group of a nonwoven fabric, a woven fabric, a net and a microporous film is laminated on the combined fiber nonwoven fabric side of the laminate. Thus, the combined fiber nonwoven fabric side is not exposed onto the surface, and therefore the processability is further improved. Moreover, at least one layer selected from the group of a nonwoven fabric, a woven fabric, a net and a microporous film is laminated as a pre-collecting layer on at least one side of the laminate. Thus, a filter service life can be further improved. Such a layer is preferably formed of a nonwoven fabric produced by the carding method, the paper-making method, the air-laid method, the melt-blown method or the spun-bond method, and is not particularly limited thereto.

A producing method for further laminating at least one layer selected from the group of a nonwoven fabric, a woven fabric, a network and a microporous film on the laminate of the invention is not particularly limited, and specific examples thereof can include a method of directly spinning a combined fiber nonwoven fabric on a base material to make a laminate, and in a subsequent step, further integrally laminating at least one kind of layer selected from the group of a nonwoven fabric, a woven fabric, a network and a microporous film on the laminate, and a method of directly spinning a combined fiber nonwoven fabric on a sheet in which at least one kind of layer selected from the group of a nonwoven fabric, a woven fabric, a network and a microporous film is integrated with a base material to integrate both. The method of integration thereof is not particularly limited, and thermocompression bonding treatment by a heated flat roll or embossing roll, adhesion treatment by a hot melt agent or a chemical adhesive, thermobonding treatment by circulating hot air or radiant heat, or the like can be adopted.

The combined fiber nonwoven fabric and the laminate of the invention may be subjected to electret processing, antistatic processing, water repellent processing, hydrophilic processing, antimicrobial processing, ultraviolet absorption processing, near-infrared absorption processing, stain-proof processing or the like depending on the purpose within the range in which advantageous effects of the invention are not significantly adversely affected.

The combined fiber nonwoven fabric and the laminate of the invention can be preferably used as the filtration medium for the filter, and are not particularly limited thereto. When the combined fiber nonwoven fabric of the invention is used as the filtration medium, an application thereof is not particularly limited, and may be a gas filter used for an air conditioner, a clean room or the like, or may be a liquid filter used for filtration of waste water, a paint, abrasive particles or the like. A shape of the filter is not particularly limited, either, and may be a flat film type filter, a pleated filter subjected to pleating processing, or a depth filter wound up in a cylindrical shape. The combined fiber nonwoven fabric in the invention is the combined fiber nonwoven fabric containing the first fibers having the mean fiber diameter of less than 200 nanometers and the second fibers having the mean fiber diameter of 200 to 5000 nanometers, and therefore has the high collection efficiency, the low pressure loss, the long service life, and receives no damage such as breaking upon processing the nonwoven fabric into the filter, and allows to maintain high filtration performance derived from fine fibers.

When the combined fiber nonwoven fabric and the laminate of the invention are used as the filtration medium for the air filter, the pressure loss when air is passed at a flow rate of 5.3 cm/sec is preferably in the range of 30 to 300 Pa, further preferably in the range of 50 to 250 Pa, and still further preferably in the range of 70 to 200 Pa. If the pressure loss is 30 Pa or more, the sufficient collection efficiency is obtained. If the pressure loss is 300 Pa or less, an effect such as reduction of power consumption and reduction of a load to a fan when such a material is used as the filtration medium for the air filter is produced. Moreover, when air containing particles having a particle diameter of about 0.3 micrometer is passed at 5.3 cm/sec, the collection efficiency of the particles is preferably 90% or more, and further preferably 99% or more. Further, a PF value (=log (1−collection efficiency/100)/pressure loss×1000) is preferably 12 or more, and further preferably 15 or more. The PF value is a value used as an indicator representing magnitude of collection performance of an air filter filtration medium. As the performance is higher, the PF value is larger. The service life as the air filter is not particularly limited, and can be evaluated by deposition weight of the particles when air containing particles having a particle diameter of about 0.3 micrometer is continuously passed at a flow rate of 5.3 cm/sec and the pressure loss is increased by 250 Pa. As the deposition weight is larger, such a case means that the combined fiber nonwoven fabric can be used as the air filter filtration medium having a longer service life. The collected particles may be solid particles of sodium chloride or the like, or may be poly-α-olefin or dioctyl phthalate liquid particles. The deposition weight when the poly-α-olefin is used is not particularly limited, and is preferably 15 mg/100 $cm^2$ or more, further preferably 20 mg/100 $cm^2$ or more, and still further preferably 30 mg/100 $cm^2$ or more. The collection efficiency, the pressure loss, the PF value and the deposition weight can be adjusted by appropriately changing the mean fiber diameter, the basis weight or the proportion of the number of the first fibers and the second fibers.

The combined fiber nonwoven fabric of the invention is preferably produced according to an electrostatic spinning method, and is not particularly limited thereto. Ultrafine fibers can be uniformly spun and excellent filter characteristics can be obtained by using the electrostatic spinning method. The electrostatic spinning method means a method of jetting a spinning solution and simultaneously acting an electric field thereon to form fibers from the spinning solution jetted, and collecting nanofibers in submicron order on a collector in a nonwoven fabric shape. An electrostatic spinning system is not particularly limited, and specific examples thereof include a generally known system such as a needle system in which one or a plurality of needles are used, an air-blown system in an air flow is blown to a needle tip to improve productivity per needle, a multi-hole spinneret system in which a plurality of solution jet holes are provided for one spinneret, a free surface system in which cylindrical or spiral-wire rotating electrodes half-immersed into a solution tank are used, and an electrobubble system in which electrostatic spinning is performed with bubbles formed on a surface of a polymer solution by fed air as starting points, and the system can be appropriately selected in view of required quality, productivity or operability of the nanofibers. As the electrostatic spinning method of the combined fiber nonwoven fabric in the invention, the needle system, the air-blown system or the multi-hole spinneret system is particularly preferred.

The spinning solution is not particularly limited, as long as the solution has stringiness, and a solution in which a resin is dispersed into a solvent, a solution in which a resin is dissolved in a solvent, and a solution in which a resin is melted by heat or laser irradiation can be used. In order to obtain significantly fine uniform fibers, the solution in which the resin is dissolved in the solvent is preferably used as the spinning solution.

Specific examples of the solvent into which the resin is dissolved include water, methanol, ethanol, propanol, acetone, N,N-dimethylformamide, N,N-dimethylacetamide, dimethyl sulfoxide, N-methyl-2-pyrrolidone, toluene, xylene, pyridine, formic acid, acetic acid, tetrahydrofuran, dichloromethane, chloroform, 1,1,2,2-tetrachloroethane, 1,1,1,3,3,3-hexafluoroisopropanol, trifluoroacetic acid and a mixture thereof. A mixing ratio when the solvents are mixed and used is not particularly limited, and can be appropriately set in view of required stringiness or dispersibility, and physical properties of the fibers obtained.

A surfactant may be further incorporated into the spinning solution for the purpose of improving stability and fiber-forming properties of electrostatic spinning. Specific examples of the surfactant include an anionic surfactant such as sodium dodecyl sulfate, a cationic surfactant such as brominated tetrabutylammonium, and a nonionic surfactant such as polyoxyethylene sorbitan monolaurate. A concentration of the surfactant is preferably in the range of 5% by weight based on the spinning solution. If the concentration is 5% by weight or less, improvement in an effect in accordance with intended use is obtained, and therefore such a case is preferred.

A component other than the above component, such as a hydrophilizing agent, a water repellent agent, a weathering agent and a stabilizer may be also contained therein as the component of the spinning solution within the range in which the advantageous effects of the invention are not significantly adversely affected.

A preparing method of the spinning solution is not particularly limited, and specific examples thereof can include a method such as stirring and ultrasonic treatment. Moreover, order of mixing is not particularly limited, either, and the components may be simultaneously mixed or may be successively mixed. A stirring time when the spinning solution is prepared by stirring is not particularly limited, either, if the resin is uniformly dissolved or dispersed in the solvent, and stirring may be performed for about 1 to 24 hours, for example.

In order to obtain the fibers by electrostatic spinning, viscosity of the spinning solution is preferably adjusted in the range of 10 to 10,000 cP, and further preferably in the range of 50 to 8000 cP. If the viscosity is 10 cP or more, the stringiness for forming the fibers is obtained. If the viscosity is 10,000 cP or less, jetting of the spinning solution is facilitated. If the viscosity is in the range of 50 to 8000 cP, favorable stringiness is obtained in a wide range of spinning conditions, and therefore such a case is further preferred. The viscosity of the spinning solution can be adjusted by appropriately changing molecular weight or a concentration fiber-forming materials, a kind of a solvent and a mixing ratio thereof.

A temperature of the spinning solution is not particularly limited, and may be an ordinary temperature (about 26° C.), or may be a temperature higher or lower than the ordinary temperature by heating or cooling. Specific examples of a method of jetting the spinning solution include a method of jetting a spinning solution filled in a syringe from a nozzle by using a pump. An inner diameter of the nozzle is not particularly limited, and is preferably in the range of 0.1 to 1.5 millimeters. Moreover, a jetting amount is not particularly limited, and is preferably 0.1 to 10 mL/hr.

A method of acting the electric field on the spinning solution is not particularly limited, if the electric field can be formed to the nozzle and the collector, and a high voltage may be applied to the nozzle and the collector may be grounded, for example. A voltage to be applied thereto is not particularly limited, if the fibers are formed, and is preferably in the range of 5 to 1000 kV. Moreover, a distance between the nozzle and the collector is not particularly limited, if the fibers are formed, and is preferably in the range of 5 to 50 centimeters. The collector may be a collector that can collect spun fibers, and a raw material, a shape and the like thereof are not particularly limited. As the raw material of the collector, a conductive material such as metal is preferably used. The shape of the collector is not particularly limited, and specific examples thereof can include a flat plate shape, a shaft shape and a conveyor shape. If the collector has the plat plate shape, the collector can collect a fiber aggregate in a sheet form. If the collector has the shaft shape, the collector can collect the fiber aggregate in a tube shape. If the collector has the conveyer shape, the fiber aggregate collected in the sheet form can be continuously produced. A collecting method of the combined fiber nonwoven fabric in the invention is not particularly limited, and specific examples thereof can include a method in a drum-shaped rotating collector is used to arrange needles jetting first fibers and needles jetting second fibers in a direction horizontal to a direction of rotation, thereby traversing each needle in a direction vertical to the direction of rotation, a method in which a conveyor-shaped collector is used to arrange each needle or a multi-hole spinneret in a direction vertical to a conveyor movable direction, thereby traversing each needle or the multi-hole spinneret in a direction vertical to a conveyor movable direction, and a method in which a multi-hole spinneret in which holes are arranged so as to alternately jet a spinning solution of first fibers and a spinning solution of second fibers is used. When the drum-shaped rotating collector is used, specific examples of the range can include a diameter of a drum-shaped rotating collector of 50 to 300 millimeters, the number of revolutions of 10 to 3000 rpm, an inter-needle distance of 1.5 to 20.0 centimeters, a traverse width of 100 to 500 millimeters, a traverse speed of 10 to 300 mm/sec and a spinning time of 0.1 to 10 hours.

EXAMPLES

Examples described below are given only for the purpose of illustration. The scope of the invention is not limited to the present Examples.

Measuring methods and definitions of physical properties described in Examples are described below.

Mean Fiber Diameter

A surface of a combined fiber nonwoven fabric was observed at a magnification of 5000 to 30,000 times by using Scanning Electron Microscope (SU-8000) made by Hitachi, Ltd., and diameters of 50 fibers were measured by using image analysis software, and a mean value of the fiber diameters of 50 fibers was taken as a mean fiber diameter, and a coefficient of variation was calculated.

Filter Performance

Pressure loss and collection efficiency when a sample of poly-α-olefin (particle diameter: 0.20 micrometer (count median particle diameter), particle concentration: 150 mg/m$^3$) was passed at a measuring flow rate of 5.3 cm/sec were measured by using Automated Filter Tester (Model 8130) made by TSI Incorporated.

Moreover, deposition weight of particles when poly-α-olefin (particle diameter: 0.20 micrometer (count median particle diameter), particle concentration: 150 mg/m$^3$) was continuously passed at a measuring flow rate of 5.3 cm/sec and the pressure loss was increased by 250 Pa was measured by using Automated Filter Tester (Model 8130) made by TSI Incorporated, and a service life of a filter was judged. As the deposition weight is larger, such a case shows a longer filter service life.

Spinning Solution 1

A spinning solution composed of 11 parts by weight of polyvinylidene fluoride (Kynar 3120-50; melting point 165° C.) made by ARKEMA S.A., 53.4 parts by weight of N,N-dimethylformamide, 35.6 parts by weight of tetrahydrofuran and 0.05 part by weight of sodium dodecyl sulfate was prepared.

Spinning Solution 2

A spinning solution composed of 13 parts by weight of polyvinylidene fluoride (Kynar 3120-50; melting point 165° C.) made by ARKEMA S.A., 52.2 parts by weight of N,N-dimethylformamide, 34.8 parts by weight of tetrahydrofuran and 0.05 part by weight of sodium dodecyl sulfate was prepared.

Spinning Solution 3

A spinning solution composed of 16 parts by weight of polyvinylidene fluoride (Kynar 3120-50; melting point 165° C.) made by ARKEMA S.A., 50.4 parts by weight of N,N-dimethylformamide, 33.6 parts by weight of tetrahydrofuran and 0.05 part by weight of sodium dodecyl sulfate was prepared.

Spinning Solution 4

A spinning solution composed of 20 parts by weight of polyvinylidene fluoride (Kynar 3120-50; melting point 165° C.) made by ARKEMA S.A., 48 parts by weight of N,N-dimethylformamide, 32 parts by weight of tetrahydrofuran and 0.05 part by weight of sodium dodecyl sulfate was prepared.

Spinning Solution 5

A spinning solution composed of 25 parts by weight of polyvinylidene fluoride (Kynar 2500-20; melting point 165° C.) made by ARKEMA S.A., 52.5 parts by weight of N,N-dimethylformamide and 22.5 parts by weight of tetrahydrofuran was prepared.

Spinning Solution 6

A spinning solution composed of 25 parts by weight of polyvinylidene fluoride (Kynar 2500-20; melting point 165° C.) made by ARKEMA S.A., 37.5 parts by weight of N,N-dimethylformamide and 37.5 parts by weight of tetrahydrofuran was prepared.

Spinning Solution 7

A spinning solution composed of 25 parts by weight of polyvinylidene fluoride (Kynar 2500-20; melting point 165° C.) made by ARKEMA S.A., 22.5 parts by weight of N,N-dimethylformamide and 52.5 parts by weight of tetrahydrofuran was prepared.

Example 1

A drum-shaped rotating collector having a diameter of 200 millimeters was used as a collection unit, and a nonwoven fabric made of polyethylene terephthalate (basis weight: 18 g/m$^2$, specific volume: 3.8 cm$^3$/g) was attached to a surface of the collector. Then, 2 needles having an inner diameter of 0.22 millimeter were attached in a direction horizontal to a direction of rotation of the rotating collector. Both a spinning solution 1 and a spinning solution 4 were fed to needle tips at 1.0 mL/hr and 1.0 mL/hr, respectively, and simultaneously a voltage of 30 kV was applied to the needles to perform electrostatic spinning of ultrafine fibers composed of polyvinylidene fluoride having different melting points. A distance between a needle tip and a grounded collector was adjusted to 15 centimeters. The number of revolutions of the drum-shaped rotating collector was adjusted to 50 rpm, and the needles were traversed in a direction vertical to the direction of rotation at a width of 200 millimeters and a speed of 100 mm/sec to perform spinning for 1 hour. Thus, a combined fiber nonwoven fabric having basis weight of 2.20 g/m$^2$ was laminated on a base material. A ratio of the number of first fibers to second fibers constituting the combined fiber nonwoven fabric was 87.8: 12.2. Filter performance of the laminate obtained showed pressure loss of 187 Pa, collection efficiency of 99.95%, a PF value of 17.75 and a filter service life of 16.2 mg/100 cm$^2$. No fluffing was caused even by rubbing a surface of the combined fiber nonwoven fabric of the laminate, and the laminate was excellent in wear resistance and processability.

Example 2

A drum-shaped rotating collector having a diameter of 200 millimeters was used as a collection unit, and a nonwoven fabric made of polyethylene terephthalate (basis weight: 18 g/m$^2$, specific volume: 3.8 cm$^3$/g) was attached to a surface of the collector. Then, 2 needles having an inner diameter of 0.22 millimeter were attached in a direction horizontal to a direction of rotation of the rotating collector. A spinning solution 1 and a spinning solution 5 were fed to needle tips at 1.0 mL/hr and 3.0 mL/hr, respectively, and simultaneously a voltage of 30 kV was applied to the needles to perform electrostatic spinning of ultrafine fibers composed of polyvinylidene fluoride having different melting points. A distance between a needle tip and a grounded collector was adjusted to 15 centimeters. The number of revolutions of the drum-shaped rotating collector was adjusted to 50 rpm, and the needles were traversed in a direction vertical to the direction of rotation at a width of 200 millimeters and a speed of 100 mm/sec to perform spinning for 1 hour. Thus, a combined fiber nonwoven fabric having basis weight of 6.49 g/m$^2$ was laminated on a base material. A ratio of the number of first fibers to second fibers constituting the combined fiber nonwoven fabric was 83.5:16.5. Filter performance of the laminate obtained showed pressure loss of 241 Pa, collection efficiency of 99.99%, a PF value of 16.52 and a filter service life of 25.9 mg/100 cm$^2$. No fluffing was caused even by rubbing a surface of the combined fiber nonwoven fabric of the laminate, and the laminate was excellent in wear resistance and processability.

Example 3

A combined fiber nonwoven fabric having basis weight of 6.39 g/m$^2$ was laminated on a base material in the same manner as in Example 2 except that a spinning solution 6 was used in place of the spinning solution 5. A ratio of the number of first fibers to second fibers constituting the combined fiber nonwoven fabric was 93.3:6.7. Filter performance of the laminate obtained showed pressure loss of 177 Pa, collection efficiency of 99.95%, a PF value of 18.44 and a filter service life of 37.6 mg/100 cm$^2$. No fluffing was caused even by rubbing a surface of the combined fiber nonwoven fabric of the laminate, and the laminate was excellent in wear resistance and processability.

Example 4

A combined fiber nonwoven fabric having basis weight of 5.73 g/m$^2$ was laminated on a base material in the same manner as in Example 2 except that a spinning solution 7 was used in place of the spinning solution 5. A ratio of the number of first fibers to second fibers constituting the combined fiber nonwoven fabric was 97.5:2.5. Filter performance of the laminate obtained showed pressure loss of 161 Pa, collection efficiency of 99.94%, a PF value of 20.19 and a filter service life of 41.7 mg/100 cm$^2$. No fluffing was caused even by rubbing a surface of the combined fiber nonwoven fabric of the laminate, and the laminate was excellent in wear resistance and processability.

Example 5

A combined fiber nonwoven fabric having basis weight of 6.42 g/m$^2$ was laminated on a base material in the same manner as in Example 3 except that a spinning solution 2 was used in place of the spinning solution 1. A ratio of the number of first fibers to second fibers constituting the combined fiber nonwoven fabric was 88.0:12.0. Filter performance of the laminate obtained showed pressure loss of 198 Pa, collection efficiency of 99.89%, a PF value of 14.89 and a filter service life of 35.3 mg/100 cm$^2$. No fluffing was caused even by rubbing a surface of the combined fiber nonwoven fabric of the laminate, and the laminate was excellent in wear resistance and processability.

Example 6

A combined fiber nonwoven fabric having basis weight of 6.79 g/m$^2$ was laminated on a base material in the same manner as in Example 3 except that a spinning solution 3 was used in place of the spinning solution 1. A ratio of the number of first fibers to second fibers constituting the combined fiber nonwoven fabric was 83.5:16.5. Filter performance of the laminate obtained showed pressure loss of 168 Pa, collection efficiency of 99.06%, a PF value of 12.08 and a filter service life of 48.8 mg/100 cm$^2$. No fluffing was caused even by rubbing a surface of the combined fiber nonwoven fabric of the laminate, and the laminate was excellent in wear resistance and processability.

Example 7

A drum-shaped rotating collector having a diameter of 200 millimeters was used as a collection unit, and a nonwoven fabric made of polyethylene terephthalate (basis weight: 18 g/m$^2$, specific volume: 3.8 cm$^3$/g) was attached to a surface of the collector. Then, 3 needles having an inner diameter of 0.22 millimeter were attached in a direction horizontal to a direction of rotation of the rotating collector. The spinning solution 1 was fed from 2 needles of the 3 needles and the spinning solution 6 was fed from the remaining 1 needle at 1.0 mL/hr and 3.0 mL/Hr, respectively, and simultaneously a voltage of 30 kV was applied to the needles to perform electrostatic spinning of ultrafine fibers composed of polyvinylidene fluoride having different melting points. A distance between a needle tip and a grounded collector was adjusted to 15 centimeters. The number of revolutions of the drum-shaped rotating collector was adjusted to 50 rpm, and the needles were traversed in a direction vertical to the direction of rotation at a width of 200 millimeters and a speed of 100 mm/sec to perform spinning for 0.5 hour. Thus, a combined fiber nonwoven fabric having basis weight of 3.66 g/m$^2$ was laminated on a base material. A ratio of the number of first fibers to second fibers constituting the combined fiber nonwoven fabric was 96.5:3.5. Filter performance of the laminate obtained showed pressure loss of 138 Pa, collection efficiency of 99.81%, a PF value of 19.60 and a filter service life of 30.5 mg/100 cm$^2$. No fluffing was caused even by rubbing a surface of the combined fiber nonwoven fabric of the laminate, and the laminate was excellent in wear resistance and processability.

Example 8

A drum-shaped rotating collector having a diameter of 200 millimeters was used as a collection unit, and a nonwoven fabric made of polyethylene terephthalate (basis weight: 18 g/m$^2$, specific volume: 3.8 cm$^3$/g) was attached to a surface of the collector. Then, 3 needles having an inner diameter of 0.22 millimeter were attached in a direction horizontal to a direction of rotation of the rotating collector. A spinning solution 6 was fed from 2 needles of the three needles and a spinning solution 1 was fed from the remaining 1 needle at 3.0 mL/hr and 1.0 mL/hr, respectively, and simultaneously a voltage of 30 kV was applied to the needles to perform electrostatic spinning of ultrafine fibers composed of polyvinylidene fluoride having different melting points. A distance between a needle tip and a grounded collector was adjusted to 15 centimeters. The number of revolutions of the drum-shaped rotating collector was adjusted to 50 rpm, and the needles were traversed in a direction vertical to the direction of rotation at a width of 200 millimeters and a speed of 100 mm/sec to perform spinning for 1 hour. Thus, a combined fiber nonwoven fabric having basis weight of 11.95 g/m$^2$ was laminated on a base material. A ratio of the number of first fibers to second fibers constituting the combined fiber nonwoven fabric was 87.5:12.5. Filter performance of the laminate obtained showed pressure loss of 245 Pa, collection efficiency of 99.98%, a PF value of 15.32 and a filter service life of 43.6 mg/100 cm$^2$. No fluffing was caused even by rubbing a surface of the combined fiber nonwoven fabric of the laminae, and the laminate was excellent in wear resistance and processability.

Comparative Example 1

A combined fiber nonwoven fabric having basis weight of 2.93 g/m$^2$ was laminated on a base material in the same manner as in Example 1 except that a spinning solution 3 was used in place of the spinning solution 4, and a spinning time was adjusted to 1.5 hours. A ratio of the number of first fibers to second fibers constituting the combined fiber nonwoven fabric was 73.3:26.7. Filter performance of the laminate obtained showed pressure loss of 364 Pa, collection efficiency of 99.999%, a PF value of 17.67 and a filter service life of 11.1 mg/100 cm$^2$. When the combined fiber nonwoven fabric of the laminate was rubbed, the combined fiber nonwoven fabric was broken. The combined fiber nonwoven fabric obtained was formed of the fibers having a mean fiber diameter of 200 nanometers or less, and therefore strength was weak and excellent processability was unable to be obtained. Moreover, the combined fiber nonwoven fabric had a dense matrix structure, and therefore the filter service life was conceivably shortened.

Comparative Example 2

A combined fiber nonwoven fabric having basis weight of 1.84 g/m$^2$ was laminated on a base material in the same manner as in Example 3 except that a spinning time was adjusted to 0.3 hour. A ratio of the number of first fibers to second fibers constituting the combined fiber nonwoven fabric was 93.3:6.7. Filter performance of the laminate obtained showed pressure loss of 51 Pa, collection efficiency of 88.62%, a PF value of 18.52 and a filter service life of 37.1 mg/100 cm$^2$. When the combined fiber nonwoven fabric of the laminate was rubbed, fluffing was caused a little. The basis weight was as low as 1.84 g/m$^2$, and therefore the collection efficiency and the processability were conceivably reduced.

Comparative Example 3

A combined fiber nonwoven fabric having basis weight of 7.20 g/m$^2$ was laminated on a base material in the same manner as in Example 3 except that a spinning solution 4 was used in place of the spinning solution 1. A ratio of the number of first fibers to second fibers constituting the combined fiber nonwoven fabric was 65.9:34.1. Filter performance of the laminate obtained showed pressure loss of 121 Pa, collection efficiency of 91.13%, a PF value of 8.67 and a filter service life of 80.8 mg/100 cm$^2$. When the combined fiber nonwoven fabric of the laminate was rubbed, no fluffing was caused and the laminate was significantly excellent in wear resistance and processability. However, the mean fiber diameter of the first fibers was large, and therefore a satisfactory PF value was conceivably unable to be obtained.

Comparative Example 4

A drum-shaped rotating collector having a diameter of 200 millimeters was used as a collection unit, and a nonwoven fabric made of polyethylene terephthalate (basis weight: 18 g/m$^2$, specific volume: 3.8 cm$^3$/g) was attached to a surface of the collector. A spinning solution 1 was fed to needle tips having an inner diameter of 0.22 millimeter at 1.0 mL/hr by a syringe pump, and simultaneously a voltage of 30 kV was applied to the needles to form ultrafine fibers composed of polyvinylidene fluoride by electrostatic spinning. A distance between a needle tip and a grounded collector was adjusted to 15 centimeters. The number of revolutions of the drum-shaped rotating collector was adjusted to 50 rpm, and the needles were traversed in a direction vertical to a rotating direction at a width of 200 millimeters and a speed of 100 mm/sec to perform spinning for 1 hour. Thus, a combined fiber nonwoven fabric having basis weight of 0.79 g/m$^2$ was laminated on a base material. A mean fiber diameter and a coefficient of variation of the fibers constituting the ultrafine fiber nonwoven fabric were 80 nanometers and 0.36, respectively. Filter performance of the laminate obtained showed pressure loss of 131 Pa, collection efficiency of 99.83%, a PF value of 21.26 and a filter service life of 8.7 mg/100 cm$^2$.

Comparative Example 5

An ultrafine fiber nonwoven fabric having basis weight of 0.94 g/m$^2$ was laminated on a base material in the same manner as in Comparative Example 4 except that a spinning solution 2 was used in place of the spinning solution 1. A mean fiber diameter and a coefficient of variation of fibers constituting the ultrafine fiber nonwoven fabric were 120 nanometers and 0.29, respectively. Filter performance of the laminate obtained showed pressure loss of 123 Pa, collection efficiency of 99.04%, a PF value of 16.34 and a filter service life of 11.1 mg/100 cm$^2$.

Comparative Example 6

An ultrafine fiber nonwoven fabric having basis weight of 1.17 g/m$^2$ was laminated on a base material in the same manner as in Comparative Example 4 except that a spinning solution 3 was used in place of the spinning solution 1. A mean fiber diameter and a coefficient of variation of fibers constituting the ultrafine fiber nonwoven fabric were 160 nanometers and 0.27, respectively. Filter performance of the laminate obtained showed pressure loss of 115 Pa, collection efficiency of 97.85%, a PF value of 14.56 and a filter service life of 14.8 mg/100 cm$^2$.

Comparative Example 7

An ultrafine fiber nonwoven fabric having basis weight of 1.46 g/m$^2$ was laminated on a base material in the same manner as in Comparative Example 4 except that a spinning solution 4 was used in place of the spinning solution 1. A mean fiber diameter and a coefficient of variation of fibers constituting the ultrafine fiber nonwoven fabric were 290 nanometers and 0.34, respectively. Filter performance of the laminate obtained showed pressure loss of 57 Pa, collection efficiency of 75.70%, a PF value of 10.86 and a filter service life of 39.3 mg/100 cm$^2$.

Comparative Example 8

A drum-shaped rotating collector having a diameter of 200 millimeters was used as a collection unit, and a nonwoven fabric made of polyethylene terephthalate (basis weight: 18 g/m$^2$, specific volume: 3.8 cm$^3$/g) was attached to a surface of the collector. A spinning solution 3 was fed to needle tips having an inner diameter of 0.22 millimeter at 3.0 mL/hr by a syringe pump, and simultaneously a voltage of 30 kV was applied to needles to perform electrostatic spinning of ultrafine fibers composed of polyvinylidene fluoride. A distance between a needle tip and a grounded collector was adjusted to 15 centimeters. The number of revolutions of the drum-shaped rotating collector was adjusted to 50 rpm, and the needles were traversed in a direction vertical to a direction of rotation at a width of 200 millimeters and a speed of 100 mm/sec to perform spinning for 1 hour. Thus, a combined fiber nonwoven fabric having basis weight of 5.73 g/m² was laminated on a base material. A mean fiber diameter and a coefficient of variation of the fibers constituting the ultrafine fiber nonwoven fabric were 1310 nanometers and 0.13, respectively. Filter performance of the laminate obtained showed pressure loss of 34 Pa, collection efficiency of 33.10%, a PF value of 5.13, and a filter service life was unable to be measured because the filter was hard to be clogged.

With regard to the combined fiber nonwoven fabrics in Examples 1 to 8 and Comparative Examples 1 to 3, and the ultrafine fiber nonwoven fabrics in Comparative Examples 4 to 10, the mean fiber diameter and the coefficient of variation of the first fibers, the mean fiber diameter and the coefficient of variation of the second fibers, the ratio of the number of the first fibers to the second fibers, the basis weight, the pressure loss, the collection efficiency, the PF value and the filter service life are shown in Table 1.

TABLE 1

| | First fibers | | Second fibers | | Ratio of the number of first fibers to second fibers | Basis weight of combined fiber nonwoven fabric g/m² | Pressure loss Pa | Collection efficiency % | PF value 1/Pa | Filter service life mg/100 cm² |
|---|---|---|---|---|---|---|---|---|---|---|
| | Mean fiber diameter nm | Coefficient of variation | Mean fiber diameter nm | Coefficient of variation | | | | | | |
| Example 1 | 80 | 0.36 | 290 | 0.34 | 87.8:12.2 | 2.20 | 187 | 99.95 | 17.75 | 16.2 |
| Example 2 | 80 | 0.36 | 470 | 0.41 | 83.5:16.5 | 6.49 | 241 | 99.99 | 16.52 | 25.9 |
| Example 3 | 80 | 0.36 | 780 | 0.32 | 93.3:6.7 | 6.39 | 177 | 99.95 | 18.44 | 37.6 |
| Example 4 | 80 | 0.36 | 1310 | 0.13 | 97.5:2.5 | 5.73 | 161 | 99.94 | 20.19 | 41.7 |
| Example 5 | 120 | 0.29 | 780 | 0.32 | 88.0:12.0 | 6.42 | 198 | 99.89 | 14.89 | 35.3 |
| Example 6 | 160 | 0.27 | 780 | 0.32 | 83.5:16.5 | 6.79 | 168 | 99.06 | 12.08 | 48.8 |
| Example 7 | 80 | 0.36 | 780 | 0.32 | 96.5:3.5 | 3.66 | 138 | 99.81 | 19.60 | 30.5 |
| Example 8 | 80 | 0.36 | 780 | 0.32 | 87.5:12.5 | 11.95 | 245 | 99.98 | 15.32 | 43.6 |
| Comparative Example 1 | 80 | 0.36 | 160 | 0.27 | 73.3:26.7 | 2.93 | 364 | 99.999 | 17.67 | 11.1 |
| Comparative Example 2 | 80 | 0.36 | 780 | 0.32 | 93.3:6.7 | 1.84 | 51 | 88.62 | 18.52 | 37.1 |
| Comparative Example 3 | 290 | 0.34 | 780 | 0.32 | 65.9:34.1 | 7.20 | 121 | 91.13 | 8.67 | 80.8 |
| Comparative Example 4 | 80 | 0.36 | — | — | 100:0 | 0.79 | 131 | 99.83 | 21.26 | 8.7 |
| Comparative Example 5 | 120 | 0.29 | — | — | 100:0 | 0.94 | 123 | 99.04 | 16.34 | 11.1 |
| Comparative Example 6 | 160 | 0.27 | — | — | 100:0 | 1.17 | 115 | 97.85 | 14.56 | 14.8 |
| Comparative Example 7 | — | — | 290 | 0.34 | 0:100 | 1.46 | 57 | 75.70 | 10.86 | 39.3 |
| Comparative Example 8 | — | — | 470 | 0.41 | 0:100 | 5.73 | 119 | 94.98 | 10.96 | 58.2 |
| Comparative Example 9 | — | — | 780 | 0.32 | 0:100 | 5.73 | 66 | 50.90 | 4.66 | 102.9 |
| Comparative Example 10 | — | — | 1310 | 0.13 | 0:100 | 5.75 | 34 | 33.10 | 5.13 | — |

470 nanometers and 0.41, respectively. Filter performance of the laminate obtained showed pressure loss of 119 Pa, collection efficiency of 94.98%, a PF value of 10.96 and a filter service life of 58.2 mg/100 cm².

Comparative Example 9

An ultrafine fiber nonwoven fabric having basis weight of 5.73 g/m² was laminated on a base material in the same manner as in Comparative Example 8 except that a spinning solution 6 was used in place of the spinning solution 5. A mean fiber diameter and a coefficient of variation of fibers constituting the ultrafine fiber nonwoven fabric were 780 nanometers and 0.32, respectively. Filter performance of the laminate obtained showed pressure loss of 66 Pa, collection efficiency of 50.90%, a PF value of 4.66 and a filter service life of 102.9 mg/100 cm².

Comparative Example 10

An ultrafine fiber nonwoven fabric having basis weight of 5.75 g/m² was laminated on a base material in the same manner as in Comparative Example 8 except that a spinning solution 7 was used in place of the spinning solution 5. A mean fiber diameter and a coefficient of variation of fibers

INDUSTRIAL APPLICABILITY

A combined fiber nonwoven fabric, a laminate and a filtration medium for a filter using the above materials of the invention have high dust collection efficiency, low pressure loss and a long service life, or are excellent in a balance regarding the above effects and excellent in processing strength into the filter, and therefore can be preferably used as a filtration medium for an air filter or a filtration medium for a liquid filter. In particular, the invention can provide a filtration medium preferable for an air filter for a household appliance such as a cleaner and an air cleaner, an air filter for building air conditioning, an industrial medium or high performance filter, and a clean room HEPA filter and ULPA filter.

What is claimed is:

1. A combined fiber nonwoven fabric, comprising first fibers having a mean fiber diameter of less than 200 nanometers; and second fibers having a mean fiber diameter in a range of 600 to 5000 nanometers, wherein
    the first fibers comprise a high melting point resin and an anionic surfactant or a cationic surfactant,
    the second fibers comprise a low melting point resin,
    a melting point of the high melting point resin is higher than a melting point of the low melting point resin, basis weight of the combined fiber nonwoven fabric is in a range of 2.1 to 15.0 g/m², a ratio of the number of the first fibers to the second fibers is in a range of 80:20 to 98:2, the high melting point resin is polyvinylidene fluoride, the low melting point resin is a copolymer of vinylidene fluoride and hexafluoropropylene, and a coefficient of variation of a fiber diameter of the first fibers is 0.5 or less, and a coefficient of variation of a fiber diameter of the second fibers is 0.13 or less.

2. The combined fiber nonwoven fabric according to claim 1, wherein a melting point of the first fibers is higher than a melting point of the second fibers by 10° C. or more.

3. A laminate, wherein the combined fiber nonwoven fabric according to claim 1 is laminated on at least one side of a base material having a specific volume of 5 g/cm³ or less.

4. A filtration medium, using the combined fiber nonwoven fabric according to claim 1.

5. A method of producing a combined fiber nonwoven fabric, comprising: a step of forming fibers by electrostatic spinning of a first spinning solution comprising a high melting point resin and an anionic surfactant or a cationic surfactant for forming first fibers and a second spinning solution comprising a low melting point resin for forming second fibers; and a step of mixing the first fibers formed with the second fibers formed to obtain a nonwoven fabric, wherein the second fibers have a mean fiber diameter in a range of 600 to 5000 nanometers, a melting point of the high melting point resin is higher than a melting point of the low melting point resin, a ratio of the number of the first fibers to the second fibers is in a range of 80:20 to 98:2, the high melting point resin is polyvinylidene fluoride, the low melting point resin is a copolymer of vinylidene fluoride and hexafluoropropylene, and a coefficient of variation of a fiber diameter of the first fibers is 0.5 or less, and a coefficient of variation of a fiber diameter of the second fibers is 0.13 or less.

6. A filtration medium, using the laminate according to claim 3.

* * * * *